US00RE39293E

(19) United States
(12) Reissued Patent
Gilbert et al.

(10) Patent Number: US RE39,293 E
(45) Date of Reissued Patent: Sep. 19, 2006

(54) SEPARATION OF PLASMA COMPONENTS

(75) Inventors: Andrew Mark Gilbert, Lane Cove (AU); Brendon Conlan, Binya (AU); Chenicheri Hariharam Nair, Baulkham Hills (AU)

(73) Assignee: Life Therapeutics Limited, Frenchs Forest (AU)

(21) Appl. No.: 10/632,644

(22) Filed: Aug. 1, 2003

Related U.S. Patent Documents

Reissue of:
(64) Patent No.: 6,402,913
Issued: Jun. 11, 2002
Appl. No.: 09/546,743
Filed: Apr. 11, 2000

(51) Int. Cl.
*B01D 57/02* (2006.01)

(52) U.S. Cl. ..... 204/450; 204/456; 204/451; 204/627; 204/624; 204/518

(58) Field of Classification Search ..... 204/450, 204/548, 513
See application file for complete search history.

(56) References Cited

U.S. PATENT DOCUMENTS

| | | | | |
|---|---|---|---|---|
| 3,989,613 | A | * | 11/1976 | Gritzner |
| 4,322,275 | A | | 3/1982 | Jain |
| 4,362,612 | A | | 12/1982 | Bier |
| 4,376,023 | A | | 3/1983 | Venkatsubramanian et al. |
| 4,381,232 | A | | 4/1983 | Brown |
| 4,383,923 | A | | 5/1983 | Elfert |
| 4,396,477 | A | | 8/1983 | Jain |
| 4,441,978 | A | | 4/1984 | Jain |
| 4,533,447 | A | | 8/1985 | Meldon |
| 4,608,140 | A | | 8/1986 | Goldstein |
| 4,661,224 | A | | 4/1987 | Goldstein et al. |

(Continued)

FOREIGN PATENT DOCUMENTS

| | | | |
|---|---|---|---|
| FR | A2 052391 | * | 5/1982 |
| WO | WO 97/14486 | * | 4/1997 |
| WO | WO 98/21384 | * | 5/1998 |
| WO | WO 98/43718 | * | 10/1998 |

OTHER PUBLICATIONS

Journal of Chromatopgraphy A 827 (1998) 329–325. "Purification of monoclonal antibodies from ascitic fluid using preparative electrophoresis."*

Electrophoresis 1994, 15, 968–971. Multifunctional apparatus for electrokinetic processing of proteins.*

Derwent Abstract Accession No. 85–041569/07, Class B04, 60–001134 A (Fuji rebio KK) Jan. 7, 1985.*

Derwent Abstract Accession No. 87–253908/36, Class S03, JP 62–175498 A (Nitto Electric Ind KK) Aug. 1, 1987.*

International Workshop of the University of Munich and the International Society for Artificial Organs, Rottach–Egren (FR), Mar. 17–19, 1983. Plasma Separation and Plasma Fractionation. Current status and Future Directions: Editors: M.J. Lysaght and H.J.*

*Primary Examiner*—Jill Warden
*Assistant Examiner*—Sam P. Siefke
(74) *Attorney, Agent, or Firm*—Cooley Godward LLP

(57) ABSTRACT

A method for separating components from plasma, the method comprising (I) separating the plasma into a first and second component, the first component comprising an albumin/α-1-antirypsin pool and the second component comprising plasma containing components having a molecular mass greater than albumin; (II) treating the second component to form an immunoglobulins concentrate containing immunoglobulins substantially free from components having a molecular mass less than immunoglobulins; (III) treating the immunoglobulins concentrate to remove components having a molecular mass greater than immunoglobulins; and (IV) separating albumin and α-1-antitrypsin from the albumin/α-1-antitrypsin pool.

40 Claims, 6 Drawing Sheets

1: MOLECULAR WEIGHT MARKERS
2: PLASMA
3: UPSTREAM RESIDUAL
4: DOWNSTREAM TIME ZERO
5-10: DOWNSTREAM ALBUMIN PRODUCT

U.S. PATENT DOCUMENTS

| | | | | |
|---|---|---|---|---|
| 4,673,483 | A | | 6/1987 | Mandle |
| 4,711,722 | A | | 12/1987 | Toyoshi et al. |
| 4,746,647 | A | | 5/1988 | Svenson |
| 4,780,411 | A | | 10/1988 | Piejko et al. |
| 4,897,169 | A | | 1/1990 | Bier et al. |
| 4,963,236 | A | | 10/1990 | Rodkey et al. |
| 5,043,048 | A | | 8/1991 | Muralidhara |
| 5,080,770 | A | | 1/1992 | Culkin |
| 5,082,548 | A | | 1/1992 | Faupel et al. |
| 5,087,338 | A | | 2/1992 | Perry et al. |
| 5,610,285 | A | | 3/1997 | Lebing et al. |
| 5,662,813 | A | | 9/1997 | Sammons et al. |
| 5,723,031 | A | | 3/1998 | Durr et al. |
| 5,733,442 | A | | 3/1998 | Shukla |
| 5,736,023 | A | | 4/1998 | Gallagher et al. |
| 5,868,938 | A | | 2/1999 | Bome et al. |
| 5,891,736 | A | | 4/1999 | Chapoteau et al. |
| 5,906,724 | A | | 5/1999 | Sammons et al. |
| 5,938,904 | A | | 8/1999 | Bader et al. |
| 5,986,075 | A | | 11/1999 | DuBose et al. |
| 6,093,296 | A | | 7/2000 | Soane et al. |
| 6,117,297 | A | | 9/2000 | Goldstein |
| 6,129,842 | A | | 10/2000 | Kostanian |
| 6,171,825 | B1 | | 1/2001 | Chan et al. |
| 6,464,851 | B1 | * | 10/2002 | Conlan et al. ..... 204/543 |
| 2001/0025791 | A1 | * | 10/2001 | Landau et al. ..... 204/451 |

* cited by examiner

1: MOLECULAR WEIGHT MARKERS
2: PLASMA
3: UPSTREAM RESIDUAL
4: DOWNSTREAM TIME ZERO
5-10: DOWNSTREAM ALBUMIN PRODUCT

1: MARKERS
2: PLASMA
3: UPSTREAM PHASE 1
4: IgG PRODUCT-30MIN
5: IgG PRODUCT-60MIN
6: IgG PRODUCT-90MIN

1: PLASMA
2: GRADIFLOW IgG PRODUCT
3: COMMERICIAL IgG PREPARATION

COMMERCIAL PREPARATION

GRADIFLOW PREPARATION

LANE 1; MOLECULAR WEIGHT MARKERS
LANE 2; GRADIFLOW ALBUMIN PRODUCT
LANE 3-5: UPSTREAM 1, 2 AND 3 HOURS
LANE 6: RUNNING BUFFER
LANE 7-9: α-1-ANTITRYPSIN PRODUCTS

1: PLASMA
2-4: UPSTREAM 1, 2 AND 3 HOURS
5: DOWNSTREAM ZERO
6-8: α-1-ANTITRYPSIN PRODUCT

ELASTASE NEUTRALISATION BY a1AT

SEPARATION OF PLASMA COMPONENTS

Matter enclosed in heavy brackets [ ] appears in the original patent but forms no part of this reissue specification; matter printed in italics indicates the additions made by reissue.

TECHNICAL FIELD

The present invention relates to the separation of biomolecules from plasma, particularly human plasma.

BACKGROUND ART

Human plasma contains approximately 3000 proteins with a variety of functions and potential therapeutic uses. Tight control of plasma available for blood fractionation means that the supply of important therapeutic agents like IgG is severly curtailed. This together with methodology which ends in very low yields and takes three to five days contributes to the international shortfall of major plasma fractions.

The present inventors have found that rapid isolation times, high recoveries and high-resolution make Gradiflow™ technology a viable alternative purification technology to conventional Cohn precipitation and column chromatography [1, 2].

Albumin and IgG both have enormous importance in medicine and therefore are of considerable commercial value. Albumin alone has an estimated annual global market value of $US1.5 billion [3]. Conventional purification protocols are cumbersome and expensive with low yields and long processing times [4].

Albumin is the most abundant protein component (50 mg/mL) in human plasma and functions to maintain whole blood volume and oncotic pressure. Albumin also regulates the transport of protein, fatty acids, hormones and drugs [4]. Clinical uses include blood volume replacement during surgery, treatment of shock, serious burns and other medical emergencies and the stabilisation of other pharmaceutical products.

Albumin has a molecular mass of 67 kDa and an isoelectric point (pI) of approximately 4.9. The protein consists of a single subunit and is globular in shape [5]. Conventional purification schemes use the Cohn ethanol precipitation method and result in only 50% recovery.

Immunoglobulin G (IgG) is the most abundant of the immunoglobulins, representing almost 70% of the total immunoglobulin component in human serum. The concentration of IgG in normal plasma is approximately 10 mg/mL [6]. The IgG plays an essential role in the immune response and have clinical uses including treatment of snake and spider bites, neurological disorders and IgG is commonly used in analytical or diagnostic kits.

The gamma-globulins have a molecular mass of approximately 150 kDa and consist of four chains, two of which are light and two of which are heavy [6]. Immunoglobulins are traditionally isolated using Cohn ethanol precipitation or alternatively affinity chromatography [7].

Alpha-1-antitrypsin is an acid glycoprotein of 54 kDa with an isoelectric point of 4.8 and is used in the treatment of hereditary emphysema [8]. Conventional purification schemes utilise a combination of Cohn fractionation and column chromatography with the major difficulty being the removal of albumin from α-1-antitrypsin preparations [9]. Current production schemes provide a yield of approximately 30% and much of this is contaminated with albumin.

The present inventors have adapted Gradiflow™ to provide an alternative technique for producing highly pure α-1-antitrypsin with a yield of above 70%. This strategy also exemplifies Gradiflow™ technology's use in isolating protease inhibitors.

Gradiflow™ Technology

Gradiflow™ technology utilises molecular characteristics of size and charge to isolate protein [1] with the resolution of two-dimensional electrophoresis and the throughput of preparative chromatography. Proteins exist as charged molecules above or below their isoelectric point (pI). In the Gradiflow™ the net charge on a macromolecule is controlled by the choice of buffer pH. The proteins are separated in an electric field by charge and/or size differences [2].

The present inventors have found that the Gradiflow™ technology can be adapted to purify a number of different biomolecular components from plasma. The present inventors have devised methodology for the rapid isolation of albumin, IgG and α-1-antitrypsin from a single volume of plasma in a four-phase process with high yield and low cost.

Disclosure of Invention

In a general aspect, the present invention relates to the sequential separation of a number of biomolecules present in a plasma sample using four major separation phases or processes.

In a first aspect, the present invention consists in a method of separating components from plasma, the method comprising the steps:

Phase I—Removal of albumin, α-1-antitrypsin and small contaminants (a) placing the plasma in a first solvent stream, the first solvent stream being separated from a second solvent stream by a first electrophoretic separation membrane having a molecular mass cut-off less than the molecular mass of albumin and a restriction membrane having a molecular mass cut-off less than the first electrophoretic separation membrane;

(b) selecting a buffer for the first solvent stream having a pH greater than the pI of albumin;

(c) applying an electric potential between the two solvent streams causing movement of albumin and α-1-antitrypsin through the first electrophoretic membrane into the second solvent stream while biomolecules having a molecular mass greater than albumin and α-1-antitrypsin are substantially retained in the first solvent stream, or if entering the first electrophoresis membrane, being substantially prevented from passing through the first electrophoresis membrane, wherein biomolecules in the plasma having a molecular mass less than albumin and α-1-antitrypsin are caused to move through the first separation membrane and the restriction membranes to a waste collection;

(d) optionally, periodically stopping and reversing the electric potential to cause movement of biomolecules having a molecular mass greater than albumin and α-1-antitrypsin having entered the first electrophoresis membrane to move back into the first solvent stream, wherein substantially not causing any albumin or α-1-antitrypsin that have entered the second solvent stream to re-enter first solvent stream;

(e) maintaining steps (c) and optionally (d) until the desired amount of albumin and α-1-antitrypsin have been collected as an albumin/α-1-antitrypsin pool and biomolecules having a molecular mass less than albumin and α-1-antitrypsin have been removed from the first solvent stream to form a treated plasma;

Phase II—Removal of large contaminants (f) placing the treated plasma in a third solvent stream, the third solvent stream being separated from a fourth solvent stream by a second electrophoretic separation membrane having a molecular mass cut-off less than the molecular mass of immunoglobulins;

(g) selecting a buffer for the third solvent stream having a pH above neutral;

(h) applying an electric potential between the third and fourth solvent streams arcing movement of biomolecules having a molecular mass less than that of immunoglobulins in the treated plasma through the second electrophoretic separation membrane into the fourth solvent stream while immunoglobulins and other biomolecules having a molecular mass greater than immunoglobulins are substantially retained in the third solvent stream, or if entering the second electrophoresis separation membrane, being substantially prevented from passing through the second electrophoresis separation membrane;

(i) optionally, periodically stopping and reversing the electric potential to cause movement of immunoglobulins and other biomolecules having a molecular mass greater than immunoglobulins having entered the second electrophoresis separation membrane to move back into the third solvent stream, wherein substantially not causing any biomolecules having a molecular mass less than immunoglobulins that have entered the fourth solvent stream to re-enter third solvent stream;

(j) maintaining steps (h) and optional (i) until the desired amount of biomolecules having a molecular mass less than immunoglobulins have been removed from the third upstream to form an immunoglobulins concentrate;

(k) removing the biomolecules from the fourth solvent steam;

Phase III—separation of immunoglobulins (l) replacing the second electrophoretic separation membrane with a third electrophoretic separation membrane having a molecular mass cut-off greater than the molecular mass of immunoglobulins;

(m) selecting a buffer for the immunoglobulins concentrate having a pH below neutral;

(n) applying an electric potential between the immunoglobulins concentrate in the third solvent stream and a fresh fourth solvent stream causing movement of immunoglobulins in the immunoglobulins concentrate in the third solvent stream though the third electrophoretic separation membrane into the fresh fourth solvent stream while biomolecules having a molecular mass greater than immunoglobulins are substantially retained in the third solvent stream, or if entering the third electrophoresis separation membrane, being substantially prevented from passing through the third electrophoresis separation membrane;

(o) optionally, periodically stopping and reversing the electric potential to cause movement of biomolecules having a molecular mass greater than immunoglobulins having entered the third electrophoresis membrane to move back into the treated third solvent stream, wherein substantially not causing any immunoglobulins that has entered the fresh fourth solvent stream to re-enter treated third solvent stream;

(p) maintaining steps (n) and optional (o) until the desired amount of immunoglobulins have been moved to the fresh fourth downstream;

Phase IV—Separation of albumin from α-1-antitrypsin (q) placing the albumin/α-1-antitrypsin concentrate in a fifth solvent stream, the fifth solvent stream being separated from a sixth solvent stream by a fourth electrophoretic separation membrane having a molecular mass cut-off less than the molecular mass of albumin;

(r) selecting a buffer for the fifth solvent stream having a pH greater than neutral;

(s) applying an electric potential between the fifth and sixth solvent streams causing movement of α-1-antitrypsin through the fourth electrophoresis separation membrane into the sixth solvent stream while albumin is substantially retained in the fifth solvent stream, or if entering the fourth electrophoresis separation membrane, being substantially prevented from passing through the fourth electrophoresis separation membrane;

(t) optionally, periodically stopping and reversing the electric potential to cause movement of albumin having entered the fourth electrophoresis separation membrane to move back into the fifth solvent stream, wherein substantially not causing any α-1-antitrypsin that has entered the sixth solvent stream to re-enter the fifth solvent stream; and (u) maintaining steps (s) and optionally (t) until the desired amount of albumin remains in the fifth solvent stream and the desired amount of α-1-antitrypsin has have been removed to the sixth solvent stream.

As the present invention is directed to the sequential separation of a number of components from plasma, the steps (q) to (u) can be carried out before steps (f) to (p). Initial steps (a) to (e) produces two products, namely albumin/α-1-antitrypsin pool in the downstream and treated plasma in the upstream. Each of these two products are processed further to produce isolated immunoglobulins, albumin and α-1-antitrypsin.

Preferably, albumin, immunoglobulins and α-1-antitrypsin are separated from a pooled human plasma sample.

The present invention is particularly suited for the separation of immunoglobulin G (IgG).

Preferably, the first electrophoresis separation membrane of step (a) has molecular mass cut-off of about 75 kDa and the restriction membrane has a molecular mass cut off of about 50 kDa. Additional membranes may be positioned before, between or after the separation and restriction membranes to further enhance the separation method.

Preferably, the buffer in step (b) has a pH of about 9. A Tris-borate buffer has been found to be particularly suitable for this separation. It will be appreciated, however, that other buffers having a suitable pH range would also be suitable.

Preferably the second electrophoresis separation membrane of step (f) has a molecular mass cut-off of about 200 kDa. The third electrophoresis separation membrane of step (l) preferably has a molecular mass cut-off of about 500 kDa.

Preferably, the buffer of the third solvent stream in step (g) has a pH of about 9 and the buffer of the treated third solvent stream of step (m) has a pH of less than about 5, more preferably about pH 4.6.

Preferably, the fourth electrophoresis separation membrane of step (q) has molecular mass cut-off of about 50 kDa.

Preferably, the buffer in step (r) has a pH of about 8.0. A Tris-borate buffer has been found to be particularly suitable for this separation. It will be appreciated, however, that other buffers having a suitable pH range would also be suitable.

A potential of 250 volts has been found to be suitable for the separation process. Other voltages, higher or lower, would also be suitable for the present invention depending on the separation membrane(s) used, volume of plasma or treated materials to be processed and the speed of separation required.

Preferably, the first and second solvent streams form part of a first Gradiflow™ apparatus and the third and fourth solvent streams form part of a second Gradiflow™ apparatus.

The purified albumin may be concentrated using a Gradiflow™ system incorporating an electrophoresis separation membrane having a molecular mass cut-off less than the molecular mass of albumin in a pH of greater than 8, preferably about pH 8.4.

The benefits of the method according to the first aspect of the present invention are the possibility of scale-up without adversely sharing the properties of the plasma components being separated.

The method according to the present invention results in yields of albumin, immunoglobulins, preferably IgG, and α-1-antitrypsin from plasma of at least 70% with a purity of at least 90% from pooled samples of plasma.

The method according to the present invention results in substantially purified or isolated albumin, immunoglobulins, preferably IgG, and α-1-antitrypsin from plasma in less than 1 day, preferably in less than 12 hours, and more preferably in less than 6 hours. The speed of separation and purity of the final components (albumin, immunoglobulins, preferably IgG, and α-1-antitrypsin) provides a great advance over the prior art methods. Not only does the method allow the processing of one sample of plasma to obtain three major components (albumin, immunoglobulins, preferably IgG, and α-1-antitrypsin), the method is fast and extremely efficient.

In a second aspect, the present invention consists in use of Gladiflow™ in the purification and/or separation of albumin, immunoglobulins, preferably IgG, and α-1-antitrypsin from plasma.

In a third aspect, the present invention consists in albumin, immunoglobulins, preferably IgG, and α-1-antitrypsin purified by the method according b the first aspect of the present invention.

In a fourth aspect, the present invention consists in use of albumin, immunoglobulins, preferably IgG, and α-1-antitrypsin according to the third aspect of the present invention in medical and veterinary applications.

The purification of individual components of plasma is an important illustration of the power of Gradiflow™ in isolating products from complex biological solutions.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

In order that the present invention may be more clearly understood preferred forms will be described with reference to the following drawings.

BRIEF DESCRIPTION OF DRAWINGS

FIG. 1, 8–16% non-reduced sodium dodecyl sulphate polyacrylamide gel electrophoresis (SDS PAGE) gel. Albumin was isolated from plasma (lane 2) by its migration through the 75 kDa separation membrane into the downstream (lanes 5–10). Smaller molecular weight contaminants dissipated through the 50 kDa restriction membrane. Albumin was harvested at 30 minute intervals for a total of 180 minutes.

Residual plasma proteins were retained in the upstream (lane 3) for subsequent IgG purification.

Figure 2:
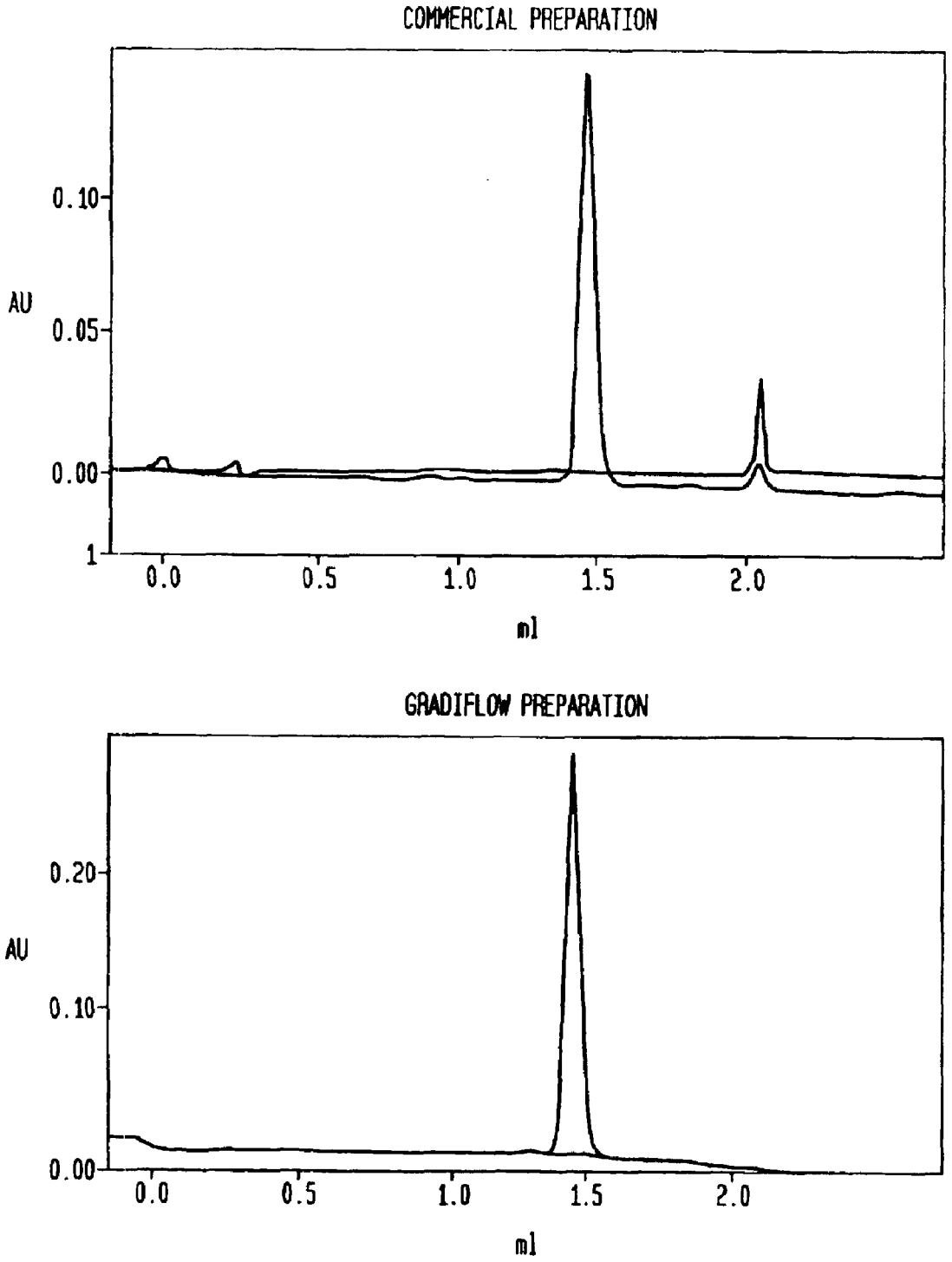

FIG. 2, size exclusion high performance liquid chromatography (HPLC).

Albumin prepared using Gradiflow™ technology was compared with a commercial therapeutic preparation. HPLC was performed using a Shimadzu SCL-10A VP HPLC system in combination with a ZORBAX GF 250 4.6×250 mm analytical column.

Samples were run at pH 7, 100 mM phosphate buffer containing 200 mM NaCl.

FIG. 3, 4–20% reduced SDS PAGE gel. Residual plasma proteins from the albumin isolation (lane 3) were further fractionated in a two-phase process, the first of which removes contaminants of less than 200 kDa. The second phase transferred the IgG component from the upstream to the downstream where it was concentrated (lanes 3–6).

Figure 4:
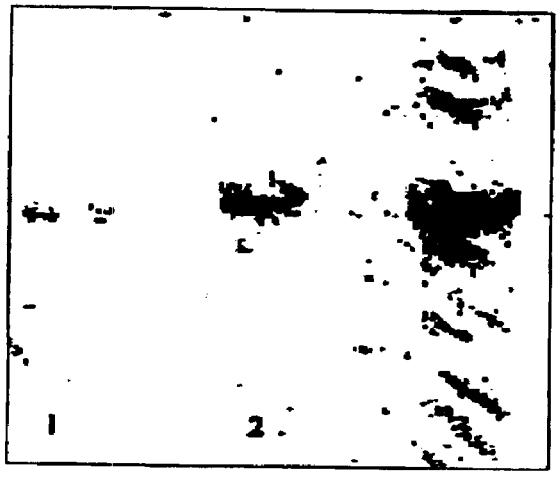

FIG. 4, Western analysis of a 4–20% reduced SDS PAGE gel. The product from phase 2 of the purification was Western blotted and incubated with DAKO anti-immunoglobulin antibody. The stained bands indicate that multiple immunoglobulin families were isolated from plasma. Further processing of the sample would allow individual families to be purified.

Figure 5:
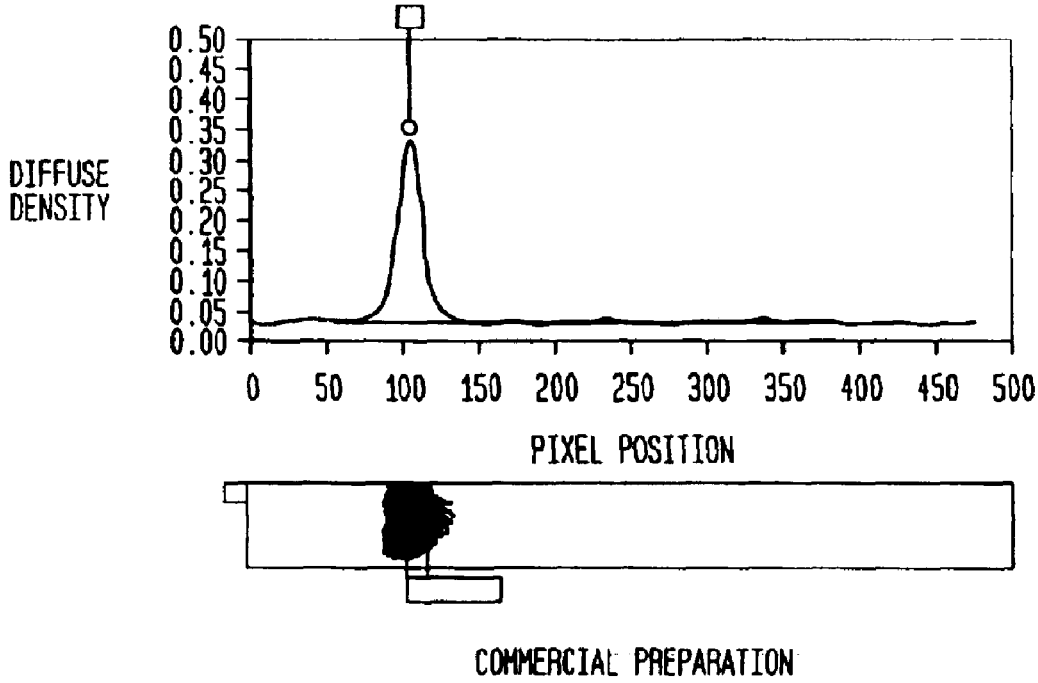
Figure 5:
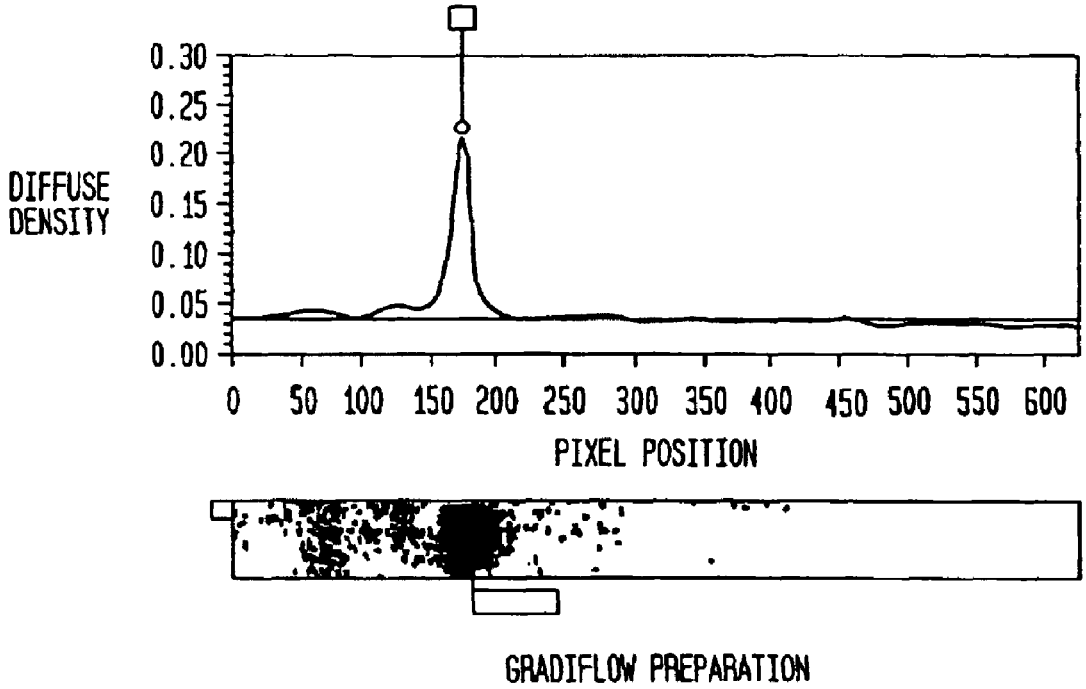

FIG. 5, Non-reduced SDS PAGE phoretix. Gladiflow™ purified IgG preparation was compared with a commercial therapeutic preparation.

FIG. 6, 8–16% non-reduced SDS PAGE. Alpha-1-antitrypsin was isolated from Gradiflow™ purified albumin (lane 2) by its migration through the 50 kDa separation membrane into the downstream (lanes 7–9). Alpha-1-antitrypsin was harvested at 60 minute intervals for a total of 180 minutes. Residual albumin was retained in the upstream (lanes 3–5).

Figure 7:
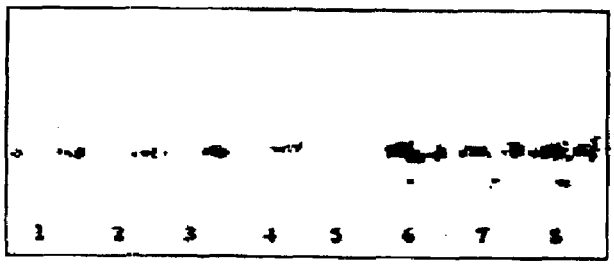

FIG. 7, Western analysis of 8–16% non-reduced SDS PAGE. Alpha-1-antitrypsin was isolated from Gradiflow™ purified albumin (lane 1) by its migration through the 50 kDa separation membrane into the downstream (lanes 6–8).

Figure 8:
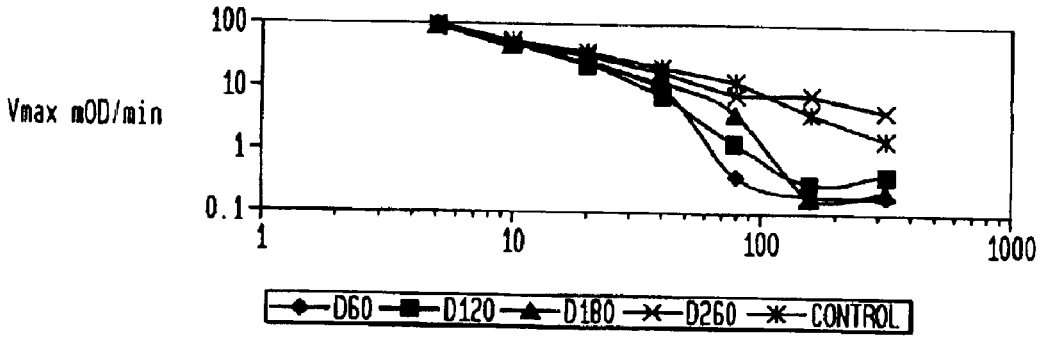

FIG. 8, α-1-antitrypsin functional analysis. Alpha-1-antitrypsin biological activity was investigated using a chromogenic elastase inhibition assay. Gladiflow™ α-1-antitrypsin fractions showed activity, in contrast to the residual albumin product.

MODES FOR CARRYING OUT THE INVENTION

Materials and Methods

Reagents

All chemicals unless otherwise stated were provided by Sigma (St Louis, Mo.). Boric Acid was obtained from ICN (Costa Mesa, Calif.). Methanol was provided by Merck (Kilsyth, Vic).

Tris-Borate (TB) Running Buffer:

6.5 g trisma base, 1.275 g boric acid, deionised $H_2O$ to 1 L, pH 9.0.

Tris-Borate (TB) Running Buffer:

7.74 g trisma base, 11.87 g boric acid, deionised $H_2O$ to 1 L, pH 8.0.

GABA-Acetic Acid Running Buffer:

3.165 g GABA, 1.08 mL acetic Acid, deionised $H_2O$ to 1 L, pH 4.6.

Gradipore Glycine Sample Buffer:

10% (w/v) SDS, 2.0 mL glycerol, 0.1% (w/v) bromophenol blue, 0.5 M tris-HCl (pH 6.8), deionised $H_2O$ to 10 mL.

Dithiothreitol (DTT):

3 mg DTT per 1 mL methanol.

SDS Glycine Running Buffer:

2.9 g tris base, 14.4 g glycine, 1 g SDS, deionised $H_2O$ to 1 L, pH 8.3.

Towbin buffer:

25 mM tris, 192 mM glycine, 20% methanol, deionised $H_2O$, pH 8.3.

Phosphate Buffered Saline (PBS):

9 g NaCl, 0.2 g $KH_2PO_4$, 2.9 g $Na_2HPO_4$, 2 g KCl, deionised $H_2O$ to 1 L, pH 7.2. 4-Chloro-1-napthol (4CN): 3 mg 4CN per mL of methanol.

Gradipure™:

Coomassie Brilliant Blue <1% w/v, ammonium sulphate ~10% w/v, orthophosphoric acid ~1% v/v, methanol ~20% v/v.

Albumin Isolation

Pooled normal plasma was diluted one part in three with Trio-borate (TB) running buffer, pH 9.0 and placed in the upstream of Gladiflow™ apparatus. Albumin was isolated from platelet free plasma in a one-phase process using the charge of albumin at a pH above its isoelectric point and its molecular weight. A separation cartridge with a 75 kDa cut-off separation membrane was placed between two 50 kDa cut-off restriction membranes. Upon application of 250 volts across the separation unit, albumin was removed from higher molecular weight contaminants by its migration through the separation membrane whilst smaller molecular weight contaminants dissipated through the 50 kDa cut-off restriction membrane. Albumin was harvested at 30 minute intervals for a total of 180 minutes.

The purity of the preparation was determined using SDS PAGE (Gradipore Tris-Glycine 8–16% gradient gels) and size exclusion HPLC.

A Bromocresol green kit (BCG) was supplied by Trace Scientific (Clayton, Melbourne, Australia) and was used to determine albumin concentration throughout the isolation procedure [10]. Analysis was performed according to manufacturer's instructions.

IgG Isolation

The upstream residual from the albumin isolation was further processed using a 200 kDa cut-off separation cartridge together with a TB running buffer, pH 9.0. A potential of 250 volts was applied across the separation unit for 1 hour. A membrane of this size, in combination with the low charge to mass ratio of IgG at pH 9, restricts IgG migration whilst allowing smaller molecular weight contaminants to pass through the membrane, leaving IgG and higher molecular weight contaminants in the upstream. A second purification phase was carried out at pH 4.6 using a 500 kDa cut-off separation membrane for 2 hours. IgG migrated through the separation membrane when 250 volts reversed polarity potential was applied, leaving other high molecular weight contaminants upstream.

Western blot analysis was carried out as described by Towbin et al (1979) [11] on selected SDS gels. Blotting filter paper and nitrocellulose blotting membrane were pre-soaked in Towbin buffer for 60 minutes. Protein transfer was performed in semi-dry blotting apparatus (Macquarie University, Sydney, Australia) at 12V for 90 minutes. The membrane was washed with PBS for 5 minutes, blocked with 1% skim milk in PBS for 10 minutes. The membrane was stained with 20 μL rabbit anti-human IgA, IgG, IgM, Kappa, Lambda conjugated to horseradish peroxidase (HRP) in 10 mL 1% skim milk solution for 60 minutes. The stain was developed with 4CN diluted one part in five in PBS to a volume of 10 mL and 10 μL $H_2O_2$. Development of the blot occurred within 30 minutes.

α-1-Antitrypsin Isolation

The downstream product of the albumin purification was further processed using a 50 kDa cut-off separation membrane together with a TB running buffer, pH 8.0. A potential of 250 volts was applied across the separation unit for 3 hours. The α-1-antitrypsin was transferred to the downstream where it was harvested hourly. Further purified albumin remained upstream. Samples were analysed for purity using SDS PAGE.

Western blot analysis was carried out as described by Towbin et al (1979) [11] on selected SDS gels. Blotting filter paper and nitrocellulose blotting membrane were pre-soaked in Towbin buffer for 60 minutes. Protein transfer was performed in semi-dry blotting apparatus (Biorad) at 15V for 60 minutes. The membrane was washed with PBS for 5 minutes, blocked with 1% skim milk in PBS/0.1% Tween 20 (v/v) for 10 minutes. The membrane was incubated with 10 μL monoclonal anti-human α-1-antitrypsin (Biodesign, Clone number 1102) in 10 mL 1% skim milk solution for 60 minutes. The membrane was then tagged with DAKO rabbit anti-mouse HRP conjugate in 1% skim milk solution for 60 minutes. The membrane was developed with 4CN diluted one part in five in PBS to a volume of 10 mL and 10 μL $H_2O_2$. Development of the blot occurred within 30 minutes.

Alpha-1-antitrypsin recovery was measured using a Behring Nephelometer 100 Analyzer (Dade Behring, Marburg, Germany). Assays were performed using rabbit anti-human α-1-antitrypsin nephelometry reagent (Dade Behring OSAZ 15) and carried out according to manufacturer's instruction.

Alpha-1-antitrypsin functionality was investigated using chromogenic elastase neutralisation assay. Elastase was diluted 1:1, 1:5, 1:10, 1:20, 1:40, 1:80, 1:160, 1:320 with pH 8.0 buffer (N.B. the stock elastase from Sigma was 32 U/ml). Fifty μl of each elastase dilution was added to 50 μl of α-1-antitrypsin sample, and shaken for 15 minutes. A control set of samples was also prepared in which each elastase dilution was combined with an equal volume of running buffer. Twenty μl of each mixture was pipetted into wells of a flat bottom microtitre plate, and 150 μl of the Pefa-ELA substrate (Pentapharm Basel, Switzerland) freshly diluted 1:100 with pH 8.0 buffer added. (N.B. each vial is reconstituted with 1 ml of DMSO and stored at +4° C.). Colour development was monitored at 37° C. in a plate reader (Versamax, Molecular Devices) for 2 hours at a wavelength of 405 nm. The kinetic analysis war made by calculating the Vmax over 20 points for each well. Plots of Vmax against elastase concentration were made on a log-log scale. The linear section of the plot was extrapolated to the x-axis to derive the concentration of antitrypsin in terms of elastase neutralisation units.

Albumin contamination was investigated using a Bromocresol green kit (BCG) supplied by Trace Scientific (Clayton, Melbourne, Australia) [10]. Analysis was performed according to manufacturer's instructions.

Anti-thrombin III contamination was investigated using an ELISA assay. One hundred μL Heparin (1.5 mg/mL) was bound to a flat-bottomed microtitre plate overnight. The plate was washed three time with 250 μL PBS/Tween 20 (0.1% v/v) before application of 50 μL anti-thrombin III standards (Sigma, St Louis, Mo.), 50 μL upstream and 50 μL downstream samples (1:10 PBS/Tween 20). The plate was incubated at room temperature for 1 hour and washed, again with PBS/Tween 20. Fifty μL DAKO rabbit anti-human anti-thrombin III (1: 1000 PBS/Tween 20) was applied and the plate incubated for a further 1 hour. The plate was then washed and 50 μL DAKO goat anti rabbit HRP conjugate applied. Washing of the plate and development using 100 μL o-toluidine followed incubation of the plate for 1 hour. Development was stopped using 50 μL 3M HCl. The plate was read at 450 nm and the samples compared to the generated standard curve.

SDS PAGE [12] was performed using Tris-glycine-SDS running buffer. SDS PAGE samples were prepared using 40 μL Gradipore glycine sample buffer, 10 μL DTT, 50 μL sample and were boiled for 5 minutes. SDS PAGE was run at 150 Volts for 90 minutes.

All SDS PAGE gels were stained with Gradipure (Gradipore, Sydney, Australia).

HPLC was performed using a Shimadzu SCL-10A VP HPLC system in combination with a ZORBAX GF 250 4.6×250 mm analytical column. Samples were run at pH 7, 100 mM phosphate buffer containing 200 mM NaCl.

Results

Albumin Isolation

Figure 1:
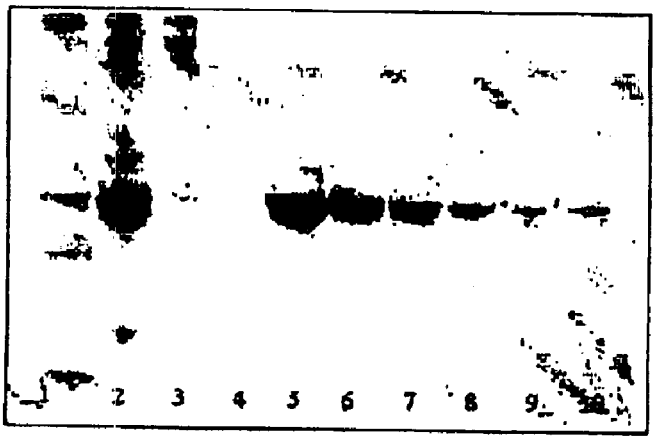

The one step purification procedure was successful in producing albumin that was greater than 95% pure with a recovery of 72%. The SDS PAGE in FIG. 1 illustrates the purification procedure. Albumin was isolated from plasma (lane 2) by its migration through the 75 kDa separation membrane into the downstream (lanes 5–10). Smaller molecular weight contaminants dissipated through the 50 kDa restriction membrane. Albumin was harvested at 30 minute intervals for a total of 180 minutes. Residual plasma proteins were retained in the upstream (lane 3) for subsequent IgG purificationAlbumin was isolated from plasma with single peak purity and compared with a commercially available therapeutic product (FIG. 2). Albumin prepared using Gradiflow™ technology was compared with a commercial therapeutic preparation. HPLC was performed using a Shimadzu SCL-10A VP HPLC system in combination with a ZORBAX GF 250 4.6×250 mm analytical column. Samples were run at pH 7, 100 mM phosphate buffer containing 200 mM NaCl. The entire purification phase took only 3 hours in duration, illustrating the rapidity of the method. The processing of the albumin preparation in the isolation of α-1-antitrypsin further increased the purity of the Gradiflow albumin product.

IgG Isolation

Figure 3:
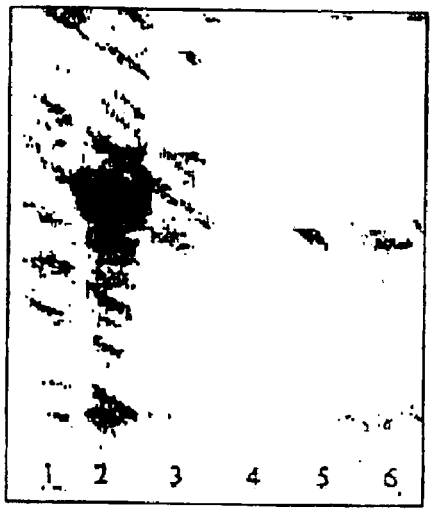

The processing of the residual upstream from the albumin separation deceased the waste of important plasma components through the process. Furthermore, the running time of the IgG isolation was decreased due to the removal of albumin in the first purification phase. FIGS. 3 and 4 show reduced SDS PAGE and a corresponding Western blot analyses illustrating the presence of the characteristic heavy and light chains of IgG. Residual plasma proteins from the albumin isolation (lane 3) were further fractionated in a two-phase process, the first of which removes contaminants of less than 200 kDa. The second phase transferred the IgG component from the upstream to the downstream where it was concentrated (lanes 3–6). The product from phase 2 of the purification was Western blotted and incubated with DAKO anti-immunoglobulin antibody. The stained bands indicate that multiple immunoglobulin families were isolated from plasma (FIG. 4). The purity of the immunoglobulin product was determined as 95–100% (FIG. 5) using PAGE phoretix. Gladiflow™ purified IgG preparation was compared with a commercial therapeutic preparation and showed similar purity and characteristics.

Figure 6:
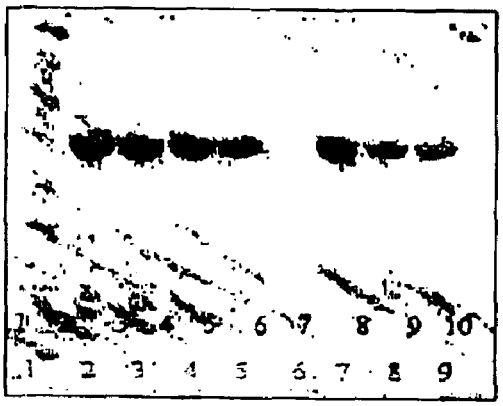

Further processing of the product would allow specific immunoglobulin families to be isolated in the process, increasing the purity of the specific groups. Immunoglobulin yield was determined using HPLC and calculated to be greater than 75%.

α-1-Antitrypsin

α-1-Antitrypsin was purified from the Gradiflow™ purified albumin preparation with a recovery of 73%. FIG. 6 illustrates the purity of α-1-antitrypsin obtainable using the present invention and in combination with the retention of biological activity provides a demonstration of the ability to purify functional proteins using Gladiflow™ technology. Alpha-1-antitrypsin was isolated from Gladiflow™ purified albumin (lane 2) by its migration through the 50 kDa separation membrane into the downstream (lanes 7–9). Alpha-1-antitrypsin was harvested at 60 minute intervals for a total of 180 minutes. Residual albumin was retained in the upstream (lanes 3–5). The removal of α-1-antitrypsin from the albumin preparation resulted in higher purity albumin and also minimised the time of isolation of α-1-antitrypsin. The other advantage of processing Gladiflow™ fractions was the reduction in waste of important plasma proteins. The retention of α-1-antitrypsin activity was demonstrated by its ability to inhibit elastase activity. No detectable activity remained in the albumin preparation.

FIG. 7 shows Western analysis of 8–16% non-reduced SDS PAGE. Alpha-1-antitrypsin was isolated from Gladiflow™ purified albumin (lane 1) by its migration through the 50 kDa separation membrane into the downstream (lanes 6–8). FIG. 8 shows α-1-antitrypsin functional analysis where α-1-antitrypsin biological activity was investigated using a chromogenic elastase inhibition assay. Gladiflow™ purified α-1-antitrypsin fractions showed activity, in contrast to the residual albumin product.

Albumin contamination of the active α-1-antitrypsin product was demonstrated to be at most 0.061 mg/mL. The need for extra albumin decontamination steps using conventional isolation techniques is minimal. The absence of antithrombin III from the α-1-antitrypsin preparation further illustrated the exceptional resolution of Gradiflow technology.

Simultaneous Separations

Current methods for plasma protein separation involve the use of Cohn fractionation, which can take from 3–5 days to separate proteins into their purified form. Using the Gradiflow™ technology it is possible to substantially reduce the separation time from three days to three hours. By linking several Gladiflow™ machines in succession it is possible to simultaneously separate several proteins to single band purity from plasma in the same three hour period required to separate each individual protein. By linking several Gradiflow™ apparatus together in series, the plasma can be separated into several different fractions with different purified proteins being collected into separate streams. Linear scalability of the Gladiflow™ allows the separation of multiple numbers of proteins in a single three hour period rather than a minimum of two to three hours per protein if only one machine is used.

Plasma, suitably diluted, is placed into the first stream in a first apparatus and separated through a 200 kDa separation membrane. The selection of the separation membrane in this step has two functions. This membrane pore size allows all the albumin and α1-antitrypsin to pass downstream where the two proteins can be further purified. Furthermore, this membrane allows all protein contaminants under 200 kDa to be removed from the immunoglobulins and other high molecular mass components which are retained in the first stream.

A second Gladiflow™ apparatus containing an 80 kDa separation membrane is used to process the downstream from the first apparatus. This membrane allows only albumin and α-1-antitrypsin to pass through into a third downstream whilst all larger contaminants are held in the second stream. A third apparatus which contains a 40 kDa separation membrane is connected to the second apparatus to process the third downstream containing albumin and α-1-antitrypsin. The selection of this membrane prevents the transfer of albumin from the third stream but allows the α-1-antitrypsin to pass through where it is collected in a fourth stream. Following this separation, substantially pure albumin remains in the third stream and substantially pure α-1-antitrypsin is collected in the fourth stream.

Once albumin and α-1-antitrypsin have been separated into their separate streams, third and fourth consecutively, IgG can then be separated from the treated first stream. This is achieved by disconnecting the first apparatus from the second and third apparatus and changing the pH of the buffer. A pH 4.6 GABA/Acetic acid buffer is suitable and the potential is reversed as per the protocol for a normal second phase IgG separation.

All three proteins, albumin, α-1-antitrypsin, and IgG, can be separated to single band purity with over 80% yield using the coupled apparatus. Both albumin and α-1-antitrypsin take about three hours to purify whilst IgG takes several hours longer due to the need to separate the three apparatus once the albumin and α-1-antitrypsin have been separated.

Conclusions

A method to rapidly purify albumin, IgG and α-1-antitrypsin from a single volume of plasma has been established. The minimisation of waste and the removal of various processing steps including ethanol precipitation and ultra-filtration demonstrate the potential of Gradiflow™ technology in the large-scale purification of blood proteins. Optimisation of the process would allow the removal of specific families and even species of the immunoglobulins. Further processing of Gradiflow™ waste fractions may allow the removal of many other important plasma molecules, providing a means by which to maximise the potential of plasma as a biopharmaceutical source. The high specificity of Gladiflow™ technology could allow specific molecules to be targeted and removed by applying suitable strategies.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Horvath S Z, Corthals G L, Wrigley C W and Margolis J. Multifunctional apparatus for electrokinetic processing of proteins. Electrophoresis 1994; 15: 968.
2. Rylatt D B, Napoli M, Ogle D, Gilbert A, Lim S and Nair C H. Electrophoretic transfer of proteins across polyacrylamide membranes. J Chrom A 1999; Accepted for publication.
3. S G Cowen, Perspectives Blood Transfusion Industry, October 1998, pp 54.
4. Allen P C, Hill E A, Stokes A M in Plasma Proteins Analytical and Preparative Techniques, Blackwell Scientific Publications, London 1977, pp. 182–189.
5. Andersson L O, in Blomback B, Lars H A (Eds), Plasma Proteins, A Wiley Interscience Publication New York, 1979, pp 43–45.
6. Bennich H in Blomback B, Lars H A (Eds), Plasma Proteins, A Wiley Interscience Publication New York, 1979, pp 122.
7. Allen P C, Hill E A, Stokes A M in Plasma Proteins Analytical and Preparative Techniques, Blackwell Scientific Publications, London 1977, pp. 178.
8. Allen P C, Hill E A, Stokes A M in Plasma Proteins Analytical and Preparative Techniques, Blackwell Scientific Publications, London 1977, pp. 210–211.
9. Allen P C, Hill E A, Stokes A M in Plasma Proteins Analytical and Preparative Techniques, Blackwell Scientific Publications, London 1977, pp. 212.
10. Doumas B T, Watson W A, Briggs H G. Albumin standards and the measurement of serum albumin with bromocresol green. Clin. Chimm. Acta, 31 (1971) p. 87.
11. Towbin H, Staehelin T and Gordon J. Electrophoretic transfer of proteins from polyacrylamide gels to nitrocellulose sheets: procedure and some applications. Proc Natl Acad Sci USA 1979; 76: 4350.
12. Laemmli U. Cleavage of structural proteins during the assembly of the head of bacteriophage T4. Nature 1970; 227: 680–685.

What is claimed is:

[1. A method of separating components from plasma, the method comprising the steps:

(a) placing the plasma in a first solvent stream, the first solvent stream being separated from a second solvent stream by a first electrophoretic separation membrane having a molecular mass cut-off less than the molecular mass of albumin and a restriction membrane having a molecular mass cut-off less than the first electrophoretic separation membrane;

(b) selecting a buffer for the firm solvent stream having a pH greater than the pI of albumin;

(c) applying an electric potential between the two solvent streams causing movement of albumin and α-1-antitrypsin through the first electrophoretic membrane into the second solvent stream while biomolecules having a molecular mass greater than albumin and α-1-antitrypsin are substantially retained in the first solvent stream, or if entering the first electrophoresis membrane, being substantially prevented from passing through the first electrophoresis membrane, wherein biomolecules in the plasma having a molecular mass less than albumin and α-1-antitrypsin are caused to move through the first separation membrane and the restriction membranes to a waste collection;

(d) optionally, periodically stopping and reversing the electric potential to cause movement of biomolecules having a molecular mass greater than albumin and α-1-antitrypsin having entered the first electrophoresis membrane to move back into the first solvent stream, wherein substantially not causing any albumin or α-1-antitrypsin that have entered the second solvent stream to re-enter first solvent stream;

(e) maintaining steps (c) and optionally (d) until the desired amount of albumin and α-1-antitrypsin have been collected as an albumin/α-1-antitrypsin pool and biomolecules having a molecular mass less than albumin and α-1-antitrypsin have been removed from the first solvent stream to form a treated plasma;

(f) placing the treated plasma in a third solvent stream, the third solvent stream being separated from a fourth solvent stream by a second electrophoretic separation membrane having a molecular mass cut-off less than the molecular mass of immunoglobulins;

(g) selecting a buffer for the third solvent stream having a pH above neutral;

(h) applying an electric potential between the third and fourth solvent streams causing movement of biomolecules having a molecular mass less than that of immunoglobulins in the treated plasma through the second electrophoretic separation membrane into the fourth solvent stream while immunoglobulins and other biomolecules having a molecular mass greater than immunoglobulins are substantially retained in the third solvent stream, or if entering the second electrophoresis separation membrane, being substantially prevented from passing through the second electrophoresis separation membrane;

(i) optionally, periodically stopping and reversing the electric potential to cause movement of immunoglobulins and other biomolecules having a molecular mass greater than immunoglobulins having entered the second electrophoresis separation membrane to move back into the third solvent stream, wherein substantially not causing any biomolecules having a molecular mass less than immunoglobulins that have entered the fourth solvent stream to re-enter third solvent stream;

(j) maintaining steps (h) and optional (i) until the desired amount of biomolecules having a molecular mass less than immunoglobulins have been removed from the third upstream to form an immunoglobulins concentrate;

(k) removing the biomolecules from the fourth solvent stream;

(l) replacing the second electrophoretic separation membrane with a third electrophoretic separation membrane having a molecular mass cut-off greater than the molecular mass of immunoglobulins;

(m) selecting a buffer for the immunoglobulins concentrate having a pH below neutral;

(n) applying an electric potential between the immunoglobulins concentrate in the third solvent stream and a fresh fourth solvent stream causing movement of immunoglobulins in the immunoglobulins concentrate in the third solvent stream through the third electrophoretic separation membrane into the fresh fourth solvent stream while biomolecules having a molecular mass greater than immunoglobulins are substantially retained in the third solvent stream, or if entering the third electrophoresis separation membrane, being substantially prevented from passing through the third electrophoresis separation membrane;

(o) optionally, periodically stopping and reversing the electric potential to cause movement of biomolecules having a molecular mass greater than immunoglobulins having entered the third electrophoresis membrane to move back into the treated third solvent stream, wherein substantially not causing any immunoglobulins that has entered the fresh fourth solvent stream to re-enter treated third solvent stream;

(p) maintaining steps (n) and optional (o) until the desired amount of immunoglobulins have been moved to the fresh fourth downstream;

(q) placing the albumin/α-1-antitrypsin concentrate in a fifth solvent stream, the fifth solvent stream being separated from a sixth solvent stream by a fourth electrophoretic separation membrane having a molecular mass cut-off less than the molecular mass of albumin;

(r) selecting a buffer for the fifth solvent stream having a pH greater than neutral;

(s) applying an electric potential between the fifth and sixth solvent streams causing movement of α-1-antitrypsin through the fourth electrophoresis separation membrane into the sixth solvent stream while albumin is substantially retained in the fifth solvent stream, or if entering the fourth electrophoresis separation membrane, being substantially prevented from passing through the fourth electrophoresis separation membrane;

(t) optionally, periodically stopping and reversing the electric potential to cause movement of albumin having entered the fourth electrophoresis separation membrane to move back into the fifth solvent stream, wherein substantially not causing any α-1-antitrypsin that has entered the sixth solvent stream to re-enter the fifth solvent stream; and (u) maintaining steps (s) and optionally (t) until the desired amount of albumin remains in the fifth solvent stream and the desired amount of α-1-antitrypsin has have been removed to the sixth solvent stream.]

[2. The method according to claim 1 wherein steps (q) to (u) are carried out after steps (a) to (e).]

[3. The method according to claim 1 wherein the plasma is a pooled human plasma sample.]

[4. The method according to claim 1 wherein the first electrophoresis separation membrane of step (a) has molecular mass cut-off of about 75 kDa and the restriction membrane has a molecular mass cut off of about 50 kDa.]

[5. The method according to claim 1 wherein the buffer in step (b) has a pH of 9.]

[6. The method according to claim 5 wherein the buffer is a Tris-borate buffer.]

[7. The method according to claim 1 wherein the second electrophoresis separation membrane of step (f) has a molecular mass cut-off of 200 kDa.]

[8. The method according to claim 1 wherein the third electrophoresis separation membrane of step (l) has a molecular mass cut-off of 500 kDa.]

[9. The method according to claim 1 wherein the buffer of the third solvent stream in step (g) has a pH of 9.]

[10. The method according to claim 1 wherein the buffer of the immunoglobulins concentrate of step (m) has a pH of less than 5.]

[11. The method according to claim 10 wherein buffer has a of pH 4.6.]

[12. The method according to claim 1 wherein the fourth electrophoresis separation membrane of step (q) has molecular mass cut-off of about 50 kDa.]

[13. The method according to claim 1 wherein the buffer of the fifth solvent stream in step (r) has a pH of 8.0.]

[14. The method according to claim 13 wherein the buffer is a Tris-borate buffer.]

[15. The method according to claim 1 wherein a potential of 250 volts is applied in steps (c), (h), (n) and (s).]

[16. The method according to claim 1 wherein the immunoglobulins are immunoglobulin G (IgG).]

[17. The method according to claim 1 wherein yields of albumin, immunoglobulins and α-1-antitrypsin from plasma are at least 70% and purity of at least 90%.]

[18. The method according to claim 1 wherein albumin, immunoglobulins and α-1-antitrypsin are separated from plasma in less than 1 day.]

[19. The method according to claim 18 wherein albumin, immunoglobulins and α-1-antitrypsin are separated from plasma in less than 12 hours.]

[20. The method according to claim 18 wherein albumin, immunoglobulins and α-1-antitrypsin are separated from plasma in less than 6 hours.]

*21. A method for separating plasma components from a plasma sample containing at least albumin, α-1-antitrypsin, and immunoglobulins, by electrophoresis, comprising:*

(*I*) *separating the plasma into a first and second component using a first electrophoretic separation membrane whereby the first component containing a mixture of albumin and α-1-antitrypsin resides on one side of the first electrophoretic separation membrane while the second component resides on the other side of the first electrophoretic separation membrane;*

(*II*) *separating the second component into third and fourth components whereby the third component containing immunoglobulins is located on one side of a second electrophoretic separation membrane, and the fourth component resides on the other side of the second separation membrane;*

(*III*) *removing material having a molecular mass greater than immunoglobulins from the third component using a third electrophoretic separation membrane whereby immunoglobulins reside on one side of the third electrophoretic separation membrane and material having a molecular mass greater than immunoglobulins reside on the other side of the third electrophoretic separation membrane; and*

(*IV*) *separating albumin from α-1-antitrypsin in the first component using a fourth separation membrane whereby α-1-antitrypsin resides on one side of the fourth electrophoretic separation membrane and albumin resides on the other side of the fourth separation membrane.*

*22. The method according to claim 21, whereby the second component contains material having a molecular mass greater than albumin.*

*23. The method according to claim 21, whereby the first component migrates through the first electrophoretic separation membrane.*

*24. The method according to claim 21, whereby the fourth component contains material having a molecular mass less than immunoglobulins contained in the third component.*

*25. The method according to claim 21, whereby α-1-antitrypsin migrates through the fourth electrophoretic separation membrane.*

*26. The method according to claim 21, whereby step (I) further comprises:*

(*a*) *placing the plasma in a first solvent stream, the first solvent stream being separated from a second solvent stream by the first electrophoretic separation membrane having a molecular mass cut-off more than the molecular mass of albumin, and the second solvent stream being further bounded by a restriction membrane having a molecular mass cut off less than the first electrophoretic separation membrane;*

(*b*) *selecting a buffer for the first solvent stream having a pH greater than the pI of albumin;*

(*c*) *applying an electric potential between the two solvent streams whereby albumin and α-1-antitrypsin migrate through the first electrophoretic membrane into the second solvent stream while material having a molecular mass greater than albumin and α-1-antitrypsin are substantially prevented from passing through the first electrophoretic membrane;*

(*d*) *optionally, periodically stopping and reversing the electric potential whereby material having a molecular mass greater than albumin and α-1-antitrypsin that have entered the first electrophoretic membrane move back into the first solvent stream, while substantially preventing albumin or α-1-antitrypsin in the second solvent stream from re-entering the first solvent stream; and*

(*e*) *maintaining steps (c) and optionally (d) until the desired amount of albumin and α-1-antitrypsin migrates into the second solvent stream.*

*27. The method according to claim 26, whereby the material having a molecular mass less than albumin and α-1-antitrypsin move through the first separation membrane and the restriction membrane.*

*28. The method according to claim 21, whereby step (II) further comprises:*

(*f*) *placing the second component in a third solvent stream, the third solvent stream being separated from a fourth solvent stream by a second electrophoretic separation membrane having a molecular mass cut-off less than the molecular mass of immunoglobulins;*

(*g*) *selecting a buffer for the third solvent stream having a pH above neutral;*

(*h*) *applying an electric potential between the third and fourth solvent streams whereby immunoglobulins from the second component are substantially prevented from passing through the second electrophoretic separation membrane thereby forming the third component while material having a molecular mass less that that of immunoglobulins in the second component migrate through the second electrophoretic separation membrane into the fourth solvent stream to form the fourth component;*

(*i*) *optionally, periodically stopping and reversing the electric potential whereby materials from the third component that have entered the second electrophoretic separation membrane move back into the third solvent stream while preventing materials from the fourth component from re-entering the third solvent stream; and*

(*j*) *maintaining steps (h) and optional (i) until the desired amount of third component has been separated from the fourth component.*

*29. The method according to claim 28 whereby step (III) further comprises:*

(*l*) *replacing the second electrophoretic separation membrane with a third electrophoretic separation membrane having a molecular mass cut-off greater than the molecular mass of immunoglobulins;*

(*m*) *selecting a buffer for the third solvent stream having a pH below neutral;*

(*n*) *replacing the fourth solvent stream with a fresh fourth solvent stream;*

(*o*) *applying an electric potential between the third solvent stream and the fresh fourth solvent stream whereby immunoglobulins in the third component migrate through the third electrophoretic separation membrane into the fresh fourth solvent stream;*

(*p*) *optionally, periodically stopping and reversing the electric potential whereby material having a molecular mass greater than immunoglobulins in the third component that have entered the third electrophoretic membrane move back into the third solvent stream while preventing immunoglobulins in the fresh fourth solvent stream from re-entering the third solvent stream; and*

(*q*) *maintaining steps (o) and optional (p) until the desired amount of immunoglobulins migrate to the fresh fourth solvent stream.*

*30. The method according to claim 21, whereby step (IV) further comprises:*

(*r*) *placing the first component in a fifth solvent stream, the fifth solvent stream being separated from a sixth*

*solvent stream by a fourth electrophoretic separation membrane having a molecular mass cut-off less than the molecular mass of albumin;*

(*s*) *selecting a buffer for the fifth solvent stream having a pH greater than neutral;*

(*t*) *applying an electric potential between the fifth and sixth solvent streams whereby α-1-antitrypsin migrates through the fourth electrophoretic separation membrane into the sixth solvent stream while albumin is substantially prevented from passing through the fourth electrophoretic separation membrane;*

(*u*) *optionally, periodically stopping and reversing the electric potential whereby albumin that has entered the fourth electrophoretic separation membrane moves back into the fifth solvent stream while preventing α-1-antitrypsin in the sixth solvent stream from re-entering the fifth solvent stream; and*

(*v*) *maintaining steps* (*t*) *and optionally* (*u*) *until the desired amounts of albumin and α-1-antitrypsin are separated on opposite sides of the fourth separation membrane.*

*31. The method according to claim 21, further comprising using more than one electrophoretic separation apparatus.*

*32. The method according to claim 21, further comprising using three electrophoretic separation apparatus.*

*33. The method according to claim 6 whereby the first electrophoretic separation membrane of step* (*a*) *has molecular mass cut-off of about 75 kDa and the restriction membrane has a molecular mass cut off of about 50 kDa.*

*34. The method according to claim 26 whereby the first electrophoretic separation membrane of step* (*a*) *has a molecular mass cut-off greater than 67 kDa.*

*35. The method according to claim 26 whereby the buffer in step* (*b*) *has a pH of about 9.*

*36. The method according to claim 26 whereby the buffer is a Tris-borate buffer.*

*37. The method according to claim 26 whereby the electric potential applied in step* (*c*) *is 250 volts.*

*38. The method according to claim 28 whereby the second electrophoretic separation membrane of step* (*f*) *has a molecular mass cut-off of about 200 kDa.*

*39. The method according to claim 28 whereby the second electrophoretic separation membrane of step* (*f*) *has a molecular mass cut-off greater than 150 kDa.*

*40. The method according claim 28 whereby the buffer of the third solvent stream in step* (*g*) *has a pH of about 9.*

*41. The method according to claim 28 where the electric potential applied in step* (*h*) *is 250 volts.*

*42. The method according to claim 29 whereby the third electrophoretic separation membrane of step* (*l*) *has a molecular mass cut-off of about 500 kDa.*

*43. The method according to claim 29 whereby the buffer of the immunoglobulins concentrate of step* (*m*) *has a pH of less than 5.*

*44. The method according to claim 29 whereby buffer has a pH of about 4.6.*

*45. The method according to claim 29 whereby the electric potential applied in step* (*o*) *is 250 volts.*

*46. The method according to claim 30 whereby the fourth electrophoretic separation membrane of step* (*q*) *has molecular mass cut-off of about 50 kDa.*

*47. The method according to claim 30 whereby the fourth electrophoretic separation membrane of step* (*q*) *has molecular mass cut-off less than 54 kDa.*

*48. The method according to claim 30 whereby the buffer of the fifth solvent stream in step* (*r*) *has a pH of about 8.0.*

*49. The method according to claim 30 whereby the buffer is a Tris-borate buffer.*

*50. The method according to claim 30 whereby the electric potential applied in step* (*t*) *is 250 volts.*

*51. The method according to any one of claims 21–50, whereby albumin, immunoglobulin, and α-1-antitrypsin are separated from plasma.*

*52. The method according to any one of claims 21–50 whereby the immunoglobulins are immunoglobulin G* (*IgG*).

*53. The method according to any one of claims 21–50 whereby yields of albumin, immunoglobulins and α-1-antitrypsin from plasma are at least 70% and purity of at least 90%.*

*54. The method according to any one of claims 21–50 whereby albumin, immunoglobulins and α-1-antitrypsin are separated from plasma in less than 1 day.*

*55. The method according to any one of claims 21–50 whereby albumin, immunoglobulins and α-1-antitrypsin are separated from plasma in less than 12 hours.*

*56. The method according to any one of claims 21–50 whereby albumin, immunoglobulins and α-1-antitrypsin are separated from plasma in less than 6 hours.*

*57. The method according to any one of claims 21–50 whereby the plasma is a pooled human plasma sample.*

*58. The method according to claim 21, 26 or 30 whereby step* (*IV*) *is carried out after step* (*I*).

*59. A method for separating plasma components from a plasma sample by electrophoresis, comprising:*

(*I*) *separating the plasma into a first and second component in a first electrophoretic separation apparatus using a first electrophoretic separation membrane having a molecular mass cut-off of about 200 kDa, whereby the first component containing a mixture of albumin and α-1-antitrypsin resides on one side of the first electrophoretic separation membrane while the second component resides on the other side of the first electrophoretic separation membrane;*

(*II*) *removing undesired material from the first component in a second electrophoretic separation apparatus using a second electrophoretic separation membrane having a molecular mass cut-off of about 80 kDa, whereby albumin and α-1-antitrypsin reside on one side of the second electrophoretic separation membrane and the undesired material resides on the other side of the third electrophoretic separation membrane;*

(*III*) *separating albumin from α-1-antitrypsin in the first component using a third separation membrane having a molecular mass cut-off of about 40 kDa in a third electrophoretic separation apparatus, whereby α-1-antitrypsin resides on one side of the third electrophoretic separation membrane and albumin resides on the other side of the third separation membrane; and*

(*IV*) *separating the second component into third and fourth components whereby the third component containing immunoglobulins is located on one side of a fourth electrophoretic separation membrane, and the fourth component resides on the other side of the fourth separation membrane.*

*60. The method according to claim 59, whereby the first, second, and third electrophoretic separation apparatus are connected together in steps* (*I*)–(*III*), *and the first electrophoretic separation is disconnected from the second or third electrophoretic separation apparatus in step* (*IV*).

* * * * *